United States Patent
Roy et al.

(10) Patent No.: US 10,709,302 B2
(45) Date of Patent: Jul. 14, 2020

(54) SANITARY WIPE APPARATUS FOR USE ON A BEVERAGE CAN

(71) Applicants: Stephen Roy, Piscataway, NJ (US); Shane Lynch, Piscataway, NJ (US)

(72) Inventors: Stephen Roy, Piscataway, NJ (US); Shane Lynch, Piscataway, NJ (US)

( * ) Notice: Subject to any disclaimer, the term of this patent is extended or adjusted under 35 U.S.C. 154(b) by 140 days.

(21) Appl. No.: 15/915,031

(22) Filed: Mar. 7, 2018

(65) Prior Publication Data

US 2018/0255983 A1 Sep. 13, 2018

Related U.S. Application Data

(60) Provisional application No. 62/468,934, filed on Mar. 8, 2017.

(51) Int. Cl.

| | |
|---|---|
| *A47F 1/04* | (2006.01) |
| *A47K 10/42* | (2006.01) |
| *B65D 83/08* | (2006.01) |
| *A01N 25/34* | (2006.01) |
| *A61L 2/23* | (2006.01) |
| *A61L 2/26* | (2006.01) |
| *A47F 7/28* | (2006.01) |
| *A47K 10/32* | (2006.01) |

(52) U.S. Cl.
CPC ............ *A47K 10/421* (2013.01); *A01N 25/34* (2013.01); *A61L 2/23* (2013.01); *A61L 2/26* (2013.01); *B65D 83/0805* (2013.01); *A47F 1/04* (2013.01); *A47F 7/28* (2013.01); *A47K 2010/3233* (2013.01); *A47K 2010/3266* (2013.01); *A61L 2202/23* (2013.01); *B65D 2313/04* (2013.01); *B65D 2313/08* (2013.01)

(58) Field of Classification Search
None
See application file for complete search history.

(56) References Cited

U.S. PATENT DOCUMENTS

| | | | | |
|---|---|---|---|---|
| 5,540,354 | A  * | 7/1996 | Annand ............... | A47K 10/423 206/449 |
| 7,228,968 | B1 * | 6/2007 | Burgess ............. | B65D 75/5838 206/233 |
| 2003/0178436 | A1 * | 9/2003 | Ashford ............... | A47K 10/421 221/33 |
| 2009/0223993 | A1 * | 9/2009 | Lorenzati ............... | A47K 10/42 221/35 |
| 2010/0270325 | A1 * | 10/2010 | Fearon ............... | B65D 83/0805 221/45 |
| 2012/0277904 | A1 * | 11/2012 | Pritchard .................. | G07F 9/02 700/232 |
| 2013/0105506 | A1 * | 5/2013 | Frias .................... | A47K 10/421 221/45 |

\* cited by examiner

*Primary Examiner* — Gene O Crawford
*Assistant Examiner* — Ayodeji T Ojofeitimi
(74) *Attorney, Agent, or Firm* — Bruce A. Lev

(57) ABSTRACT

An improved sanitary wipe apparatus, a sterile, naturally sanitizing wipe adapted to be stored within a dispenser box and removed one-by-one for use by a person to remove anti-microbial agents from a top drinking surface of a beverage can before drinking therefrom.

7 Claims, 4 Drawing Sheets

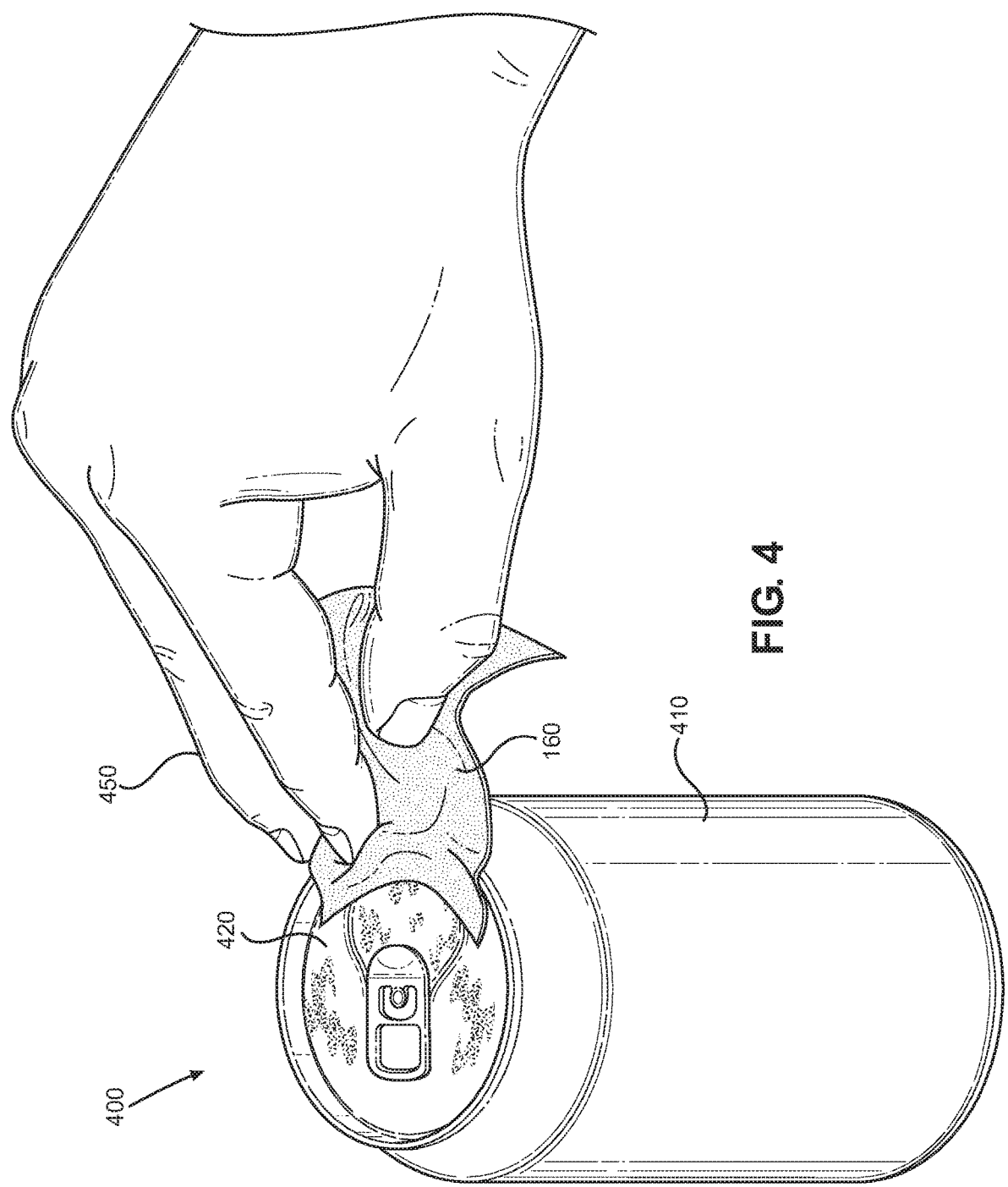

SANITARY WIPE APPARATUS FOR USE ON A BEVERAGE CAN

CROSS-REFERENCE TO RELATED APPLICATION

The present application is related to and claims priority from prior provisional application Ser. No. 62/468,934, filed Mar. 8, 2017 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of sanitary wipes and more specifically relates to an improved sanitary wipe apparatus, a sterile, naturally sanitizing wipe adapted to be stored within a dispenser box and removed one-by-one for use by a person to remove anti-microbial agents from a top drinking surface of a beverage can before drinking therefrom.

2. Description of the Related Art

Not only foods, but also canned drinks, pose a threat to consumers' health. While Internet tales of a deadly disease called "Leptospirosis"—carried in dried rat-urine supposedly found on the tops of soft-drink cans—are evidently a fiction (see: About.Com: Urban Legends), it is true that the tops of canned beverages—especially those purchased singly in convenience-stores and gas-stations—are rife with bacteria and fungi. According to a February 2013 story by the CBS affiliate Channel 11 in Fort Worth, Tex., the tops of soda cans—sample swabs from which were analyzed by a microbiologist at a local forensic laboratory, and by an infectious-diseases specialist at Baylor University—contained several types of bacteria and mold, including coliform.

According to the disease specialist, the source of the coliform bacteria could have been a rat in a warehouse, or a store-clerk who didn't wash his or her hands after a bathroom break—but in any event, it's bacteria from the large intestine of a mammal or human, and nothing you'd want to consume through your mouth! What consumers need, then, is some quick and effective means of ensuring themselves that the canned beverages they drink are safe and pathogen-free.

Various attempts have been made to solve problems found in sanitary wipes art. Among these are found in: U.S. Pub. No. 2009/0249566 to Jeremy Chalmers; U.S. Pat. No. 5,031,264 to William M. Muster; U.S. Pat. No. 4,651,890 to Gregory F. Coker et al. This prior art is representative of sanitary wipes for cleaning a top portion of a beverage can.

Ideally, an improved sanitary wipe apparatus should be user-friendly and safe in-use and yet should operate reliably and be manufactured at a modest expense. Thus, a need exists for an improved sanitary wipe apparatus, a sterile, naturally sanitizing wipe adapted to be stored within a dispenser box and removed one-by-one for use by a person to remove anti-microbial agents from a top drinking surface of a beverage can before drinking therefrom and to avoid the above-mentioned problems.

BRIEF SUMMARY OF THE INVENTION

In view of the foregoing disadvantages inherent in the known sanitary wipes art, the present invention provides an Improved Sanitary Wipe Apparatus (Entitled Improved Sanitary Wipe Apparatus for Use on a Beverage Can). The general purpose of the present invention, which will be described subsequently in greater detail is to provide an improved sanitary wipe apparatus, a sterile, naturally sanitizing wipe adapted to be stored within a dispenser box and removed one-by-one for use by a person to remove anti-microbial agents from a top drinking surface of a beverage can before drinking therefrom.

An improved sanitary wipe apparatus comprises a dispenser box and plurality of sanitary wipe members. The dispenser box includes: a bottom wall; a top wall including an aperture therethrough; and at least one side wall. Wherein at least one side wall is connected between the bottom wall and the top wall. Wherein the bottom wall, the top wall, and the at least one side wall form an interior volume.

The plurality of sanitary wipe members, each comprise a main body and an anti-microbial agent. Wherein the main body is formed from a fabric material. Wherein the end anti-microbial agent is impregnated within the fabric material and is adapted to kill and remove anti-microbial agents from a top drinking surface of a beverage can. Wherein the plurality of sanitary wipe members are adapted to be stored within the dispenser box and removed one-by-one for use by a person to remove anti-microbial agents from the top drinking surface of the beverage can before drinking therefrom.

A combination of a beverage dispenser apparatus and an improved sanitary wipe apparatus, comprising: a beverage dispenser apparatus and improved sanitary wipe apparatus. The beverage dispenser apparatus including a bottom wall; a top wall; and at least one side wall includes an aperture therethrough; and a door member. Wherein the at least one side wall is connected between the bottom wall and the top wall. Wherein the bottom wall, the top wall, and the at least one side wall form an interior volume adapted to store beverage containers therein. Wherein the door member is pivotally connected to the at least one side wall and adapted to removably cover the aperture of the at least one side wall.

The present invention holds significant improvements and serves as an Improved Sanitary Wipe Apparatus. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, an Improved Sanitary Wipe Apparatus (Entitled Improved Sanitary Wipe Apparatus for Use on a Beverage Can) constructed and operative according to the teachings of the present invention.

FIG. 4 is a perspective view illustrating the combination of a beverage dispenser apparatus and an improved sanitary wipe apparatus in an in-use condition according to an embodiment of the present invention of FIG. 1.

The various embodiments of the present invention will hereinafter be described in conjunction with the appended drawings, wherein like designations denote like elements.

DETAILED DESCRIPTION

Figure 1:
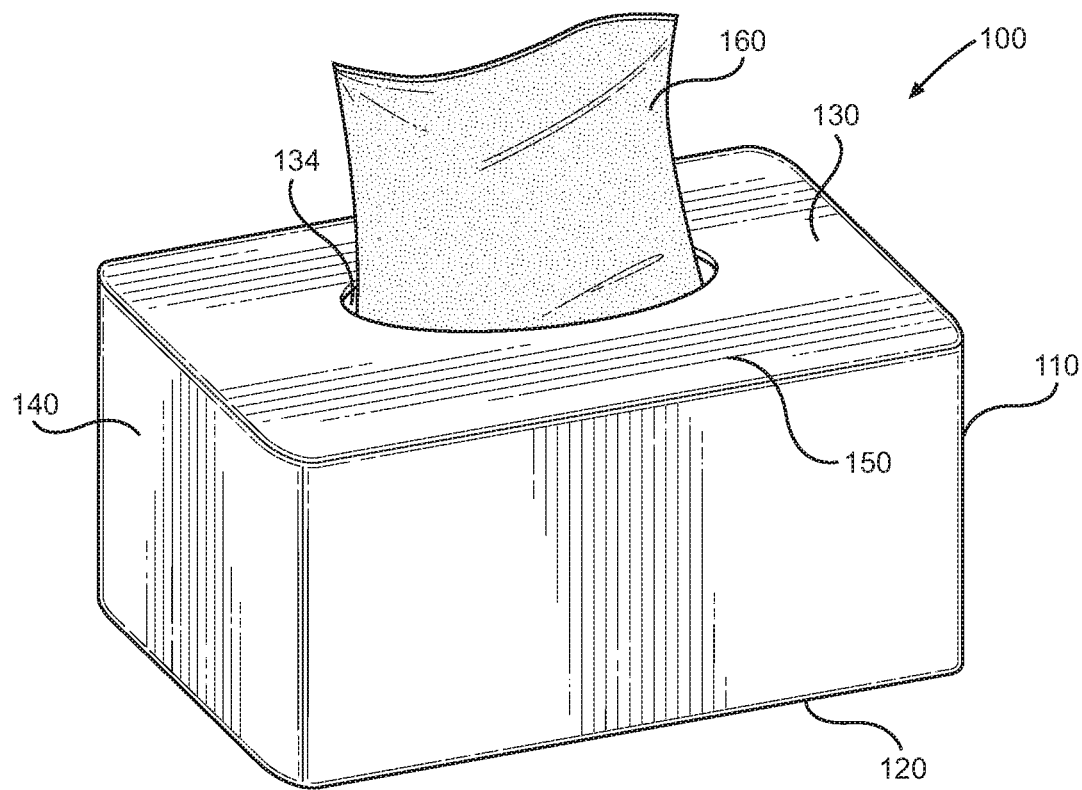
FIG. 1 shows a perspective view illustrating an Improved Sanitary Wipe Apparatus according to an embodiment of the present invention.

As discussed above, embodiments of the present invention relate to sanitary wipes and more specifically relates to an improved sanitary wipe apparatus (Entitled Improved Sanitary Wipe Apparatus for Use on a Beverage Can), a sterile, naturally sanitizing wipe adapted to be stored within a dispenser box and removed one-by-one for use by a person to remove anti-microbial agents from a top drinking surface of said beverage can before drinking therefrom Generally speaking, the Improved Sanitary Wipe Apparatus would provide consumers with a quick, effective means of thoroughly cleaning and disinfecting the tops of canned beverages, prior to consumption: a multi-unit pack of sterile, safe, disinfectant wipes equally useful in the household and wherever canned beverages are sold in single cans or six-packs.

The Improved Sanitary Wipe Apparatus would likely be fabricated in a biodegradable sanitary paper, natural textile fiber, or a biodegradable synthetic fiber, impregnated with an all-natural anti-microbial agent, safe for human consumption but lethal to the molds, other fungi, and bacteria commonly found on the tops of beverage cans. Each Healthy Wipe will be a 5-inch square.

In the home, the Improved Sanitary Wipe Apparatus could be affixed to the refrigerator door by the box's peel-and-stick backing, or simply kept in a drawer, cupboard, or on a kitchen counter. A single box of Improved Sanitary Wipe Apparatus would contain 25 individual Wipes. The Improved Sanitary Wipe Apparatus would also be marketed to convenience-stores in packages resembling baby-wipes boxes that, with peel-and stick adhesive bottoms, would simply be affixed to the doors of the store's drink-boxes or refrigerated drink sections, or be available at the check-out counter. (The Improved Sanitary Wipe Apparatus product might also include molded-plastic, aluminum, or stainless-steel dispenser boxes to be mounted permanently on drink-box and refrigerator doors, these dispensers then accommodating the disposable boxes of Improved Sanitary Wipe Apparatus.) For use in convenience stores, consumers would simply select the canned beverage of their choice, take a free Healthy Wipe from the box, clean the can top thoroughly, discard the Wipe in a trash receptacle and proceed to check-out and enjoy their drink. The stores providing the Improved Sanitary Wipe Apparatus as a service to their customers, would distinguish themselves—in the realm of service—from their competition.

In the Improved Sanitary Wipe Apparatus, consumers would have a quick, simple, convenient and reliable means of cleaning and disinfecting the tops of canned beverages prior to consumption—safe, all-natural, and formulated to destroy and remove molds, other fungi, bacteria and viruses from what may well be a contaminated can. In a time when consumers cannot be too cautious about the commercially canned food-and-drink products they ingest, the single-use, disposable, and biodegradable Improved Sanitary Wipe Apparatus should be well received.

Figure 2:
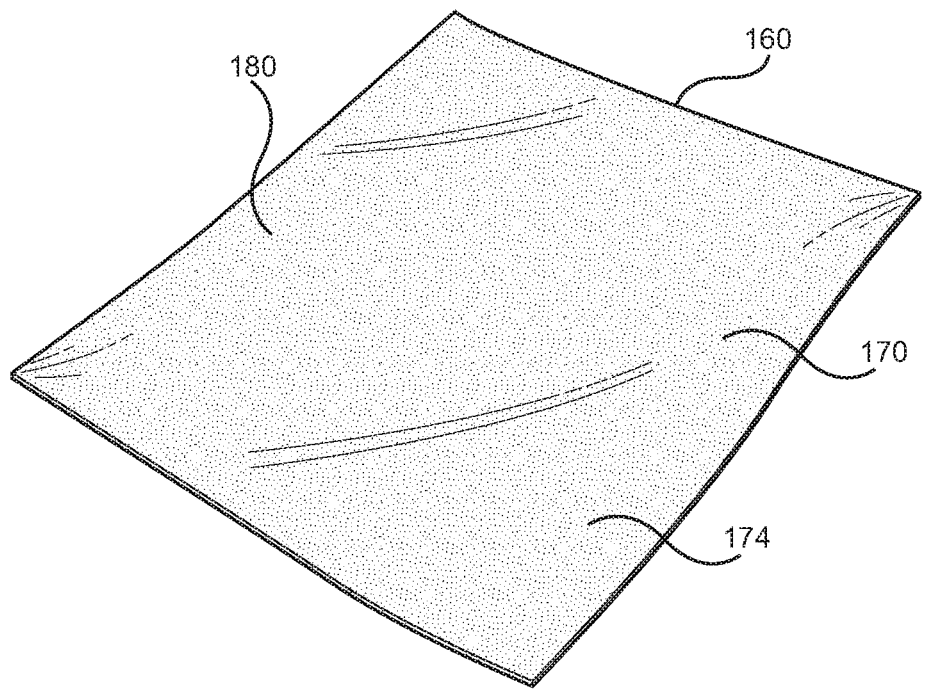
FIG. 2 is a perspective view illustrating the Improved Sanitary Wipe according to an embodiment of the present invention of FIG. 1.

Referring now to FIGS. 1-2, showing perspective views illustrating improved sanitary wipe apparatus 100 according to an embodiment of the present invention of FIG. 1.

Figure 3A:
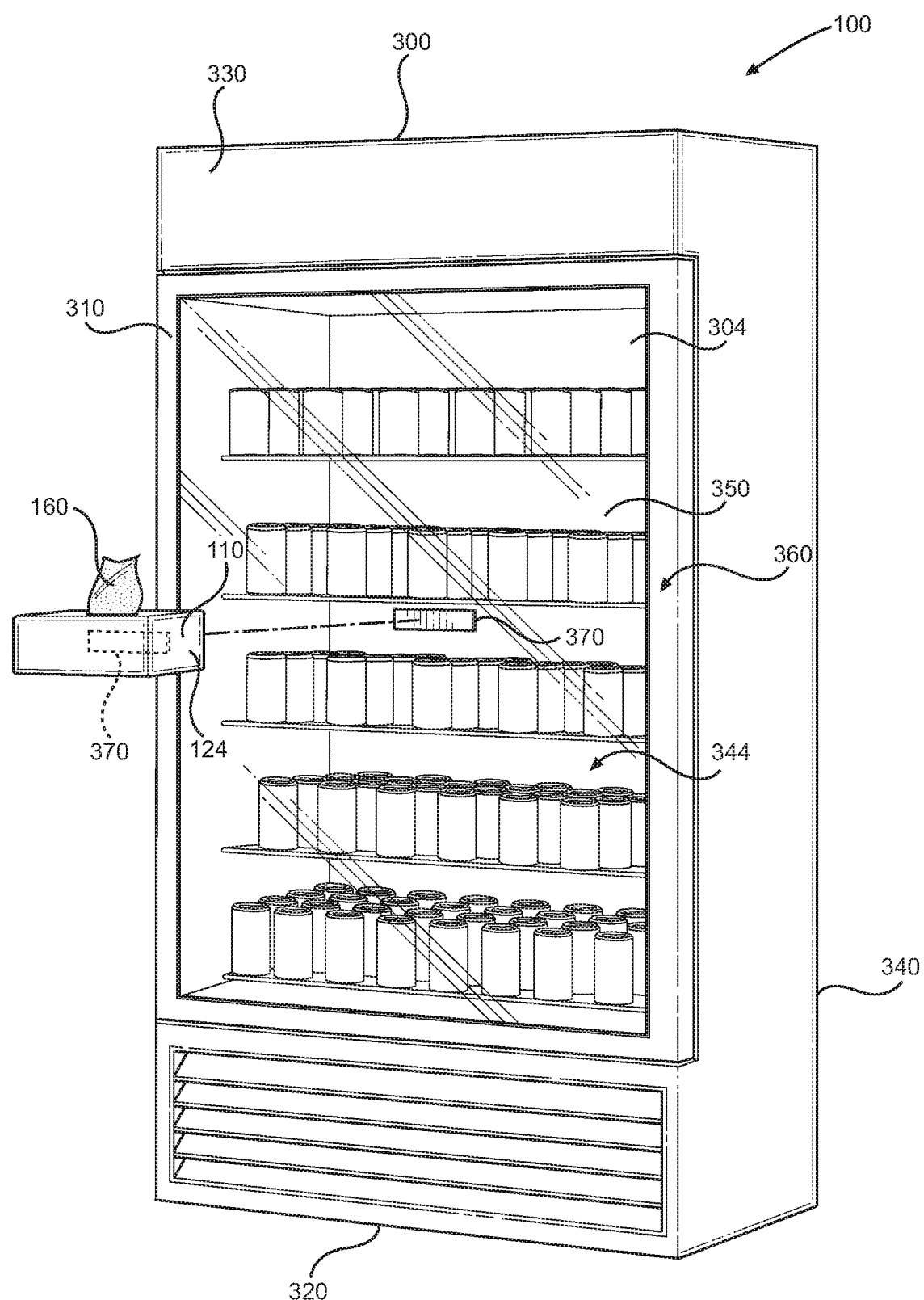
FIG. 3A is a perspective view illustrating combination of a beverage dispenser apparatus and an improved sanitary wipe apparatus having an attachment member in the form of a magnet adapted to removably attach to front surface of beverage dispenser apparatus according to an embodiment of the present invention of FIG. 1.

Improved sanitary wipe apparatus 100 is disclosed comprises dispenser box 110 and plurality of sanitary wipe members 160. Dispenser box 110 includes: bottom wall 120; top wall 130 including aperture 134 therethrough; and at least one side wall 140. Wherein at least one side wall 140 is connected between bottom wall 120 and top wall 130. Wherein bottom wall 120, top wall 130, and at least one side wall 140 form interior volume 150. Wherein dispenser box 110 is formed from a material chosen from a list of materials consisting of molded plastic, aluminum, and stainless-steel.

Wherein one of bottom wall 120 and at least one side wall 140 includes attachment member 124 adapted to removably attach to front surface 304 of beverage dispenser apparatus 310, such that plurality of sanitary wipe members 160 are accessible for use when person 450 removes beverage can 410 from beverage dispenser apparatus 310 to drink therefrom as shown in in-use condition 400 of FIG. 4. Wherein attachment member 124 is formed as magnet 370 as shown in FIG. 3A. Wherein attachment member 124 is formed as double-sided tape 380. Wherein double-sided tape 380 includes peel-and-stick backing member 384 adapted to be removed therefrom before attaching to front surface of said beverage dispenser apparatus.

Plurality of sanitary wipe members 160, each comprise main body 170 and anti-microbial agent 180. Wherein main body 170 is formed from fabric material 174. Wherein the end anti-microbial agent 180 is impregnated within fabric material 174 and is adapted to kill and remove anti-microbial agents from top drinking surface 420 of beverage can 410 as shown in FIG. 4. Wherein fabric material 174 of main body 170 of plurality of sanitary wipe members 160 may be formed from a biodegradable synthetic fiber. Wherein fabric material 174 of main body 170 of plurality of sanitary wipe members 160 may be formed from a natural textile fiber Wherein plurality of sanitary wipe members 160 are adapted to be stored within dispenser box 110 and removed one-by-one for use by person 450 to remove anti-microbial agents from top drinking surface 420 of beverage can 410 before drinking therefrom.

Figure 3B:
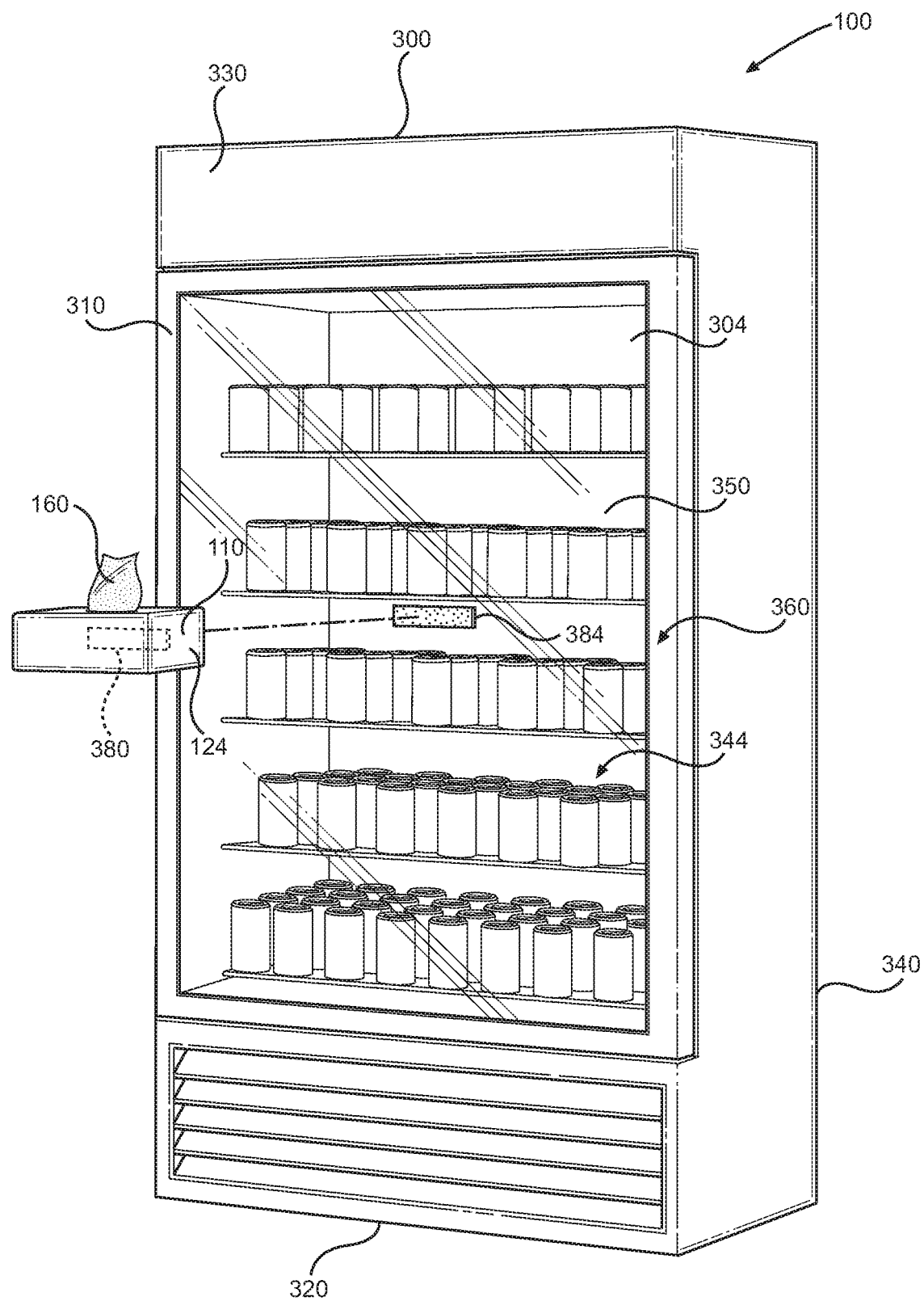
FIG. 3B is a perspective view illustrating combination of a beverage dispenser apparatus and an improved sanitary wipe apparatus having an attachment member in the form of double-sided tape adapted to removably attach to front surface of beverage dispenser apparatus according to an embodiment of the present invention of FIG. 1.

Referring now to FIGS. 3-4, showing perspective views illustrating combination 300 of beverage dispenser apparatus 310 and improved sanitary wipe apparatus 100 according to an embodiment of the present invention of FIG. 1.

Combination 300 of beverage dispenser apparatus 310 and improved sanitary wipe apparatus 100, comprising: beverage dispenser apparatus 310 and improved sanitary wipe apparatus 100. Beverage dispenser apparatus 310 including bottom wall 320; top wall 330; and at least one side wall 340 includes aperture 344 therethrough; and door member 360. Wherein the at least one side wall 340 is connected between bottom wall 320 and top wall 330. Wherein bottom wall 320, top wall 330, and at least one side wall 340 form interior volume 350 adapted to store beverage containers 410 therein. Wherein door member 360 is pivotally connected to at least one side wall 340 and adapted to removably cover aperture 344 of at least one side wall 340.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A combination of a beverage dispenser apparatus and an improved sanitary wipe apparatus, comprising:
    a beverage dispenser apparatus including:
        a bottom wall;
        a top wall; and
        at least one side wall including:
            an aperture therethrough;
            wherein said at least one side wall is connected between said bottom wall and said top wall;
            wherein said bottom wall, said top wall, and said at least one side wall form an interior volume adapted to store beverage containers therein; and
        a door member;
            wherein said door member is pivotally connected to said at least one side wall and adapted to removably cover said aperture of said at least one side wall; and
    an improved sanitary wipe apparatus comprising:
        a dispenser box including:
            a bottom wall;
            a top wall including:
                an aperture therethrough; and
            at least one side wall;
                wherein said at least one side wall is connected between said bottom wall and said top wall;
                wherein said bottom wall, said top wall, and said at least one side wall form an interior volume; and
        a plurality of sanitary wipe members, each comprising:
            a main body;
                wherein said main body is formed from a fabric material;
            an anti-microbial agent;
                wherein said end anti-microbial agent is impregnated within said fabric material, and is adapted to kill and remove anti-microbial agents from a top drinking surface of a beverage can;
            wherein said plurality of sanitary wipe members are adapted to be stored within said dispenser box and removed one-by-one for use by a person to remove anti-microbial agents from said top drinking surface of said beverage can before drinking therefrom;
        wherein one of said bottom wall and said at least one side wall of said dispenser box includes an attachment member adapted to removably attach said dispenser box to a front surface of said door of said beverage dispenser apparatus, such that said plurality of sanitary wipe members are accessible for use when a person removes a beverage can from said beverage dispenser apparatus to drink therefrom.

2. The combination of claim 1, wherein said dispenser box is formed from a material chosen from a list of materials consisting of molded plastic, aluminum, and stainless-steel.

3. The combination of claim 1, wherein said fabric material of said main body of said plurality of sanitary wipe members is formed from a natural textile fiber.

4. The combination of claim 1, wherein said fabric material of said main body of said plurality of sanitary wipe members is formed from a biodegradable synthetic fiber.

5. The combination of claim 1, wherein said attachment member is formed as a magnet.

6. The combination of claim 1, wherein said attachment member is formed as double-sided tape.

7. The combination of claim 6, wherein said double-sided tape includes a peel-and-stick backing member adapted to be removed therefrom before attaching to said front surface of said beverage dispenser apparatus.

* * * * *